United States Patent [19]

Wortrich et al.

[11] Patent Number: 5,582,601
[45] Date of Patent: Dec. 10, 1996

[54] CASSETTE FOR RECEIVING ASPIRATED FLUIDS

[75] Inventors: Theodore S. Wortrich, Long Beach; Michael H. Ekinaka, Irvine, both of Calif.

[73] Assignee: Surgin Surgical Instrumentation, Inc., Tustin, Calif.

[21] Appl. No.: 304,525

[22] Filed: Sep. 12, 1994

[51] Int. Cl.⁶ .................................................. A61M 1/00
[52] U.S. Cl. .................... 604/318; 604/320; 137/398; 137/434; 137/202
[58] Field of Search ........................... 604/317, 318, 604/319, 320, 322, 323; 222/65, 67; 137/398, 434, 202; 417/40

[56] References Cited

U.S. PATENT DOCUMENTS

| | | | |
|---|---|---|---|
| 3,945,392 | 3/1976 | Deaton et al. | 604/320 X |
| 3,965,903 | 6/1976 | Cranage | 604/320 |
| 4,306,558 | 12/1981 | Kurtz et al. | 604/320 |
| 4,773,897 | 9/1988 | Scheller et al. | |

*Primary Examiner*—Mary Beth Jones
*Attorney, Agent, or Firm*—Merchant, Gould, Smith, Edell, Welter & Schmidt

[57] ABSTRACT

A cassette for collection of fluids in a fluid aspirating system which may be reusable after sterilization. The cassette includes vacuum aperture and an aspiration port along the top wall of the cassette. Aspiration tubing is connected to the aspiration port at one end and is seated within an upstanding retainer at the proximal edge of the top wall at the opposite end. Internally, the cassette includes structures to increase flow impedance so that liquid is not drawn into the vacuum port when the fluid level rises. In addition, a pivot mechanism is disposed about a pivot hub within the chamber. A float is disposed on the pivot mechanism at a radius from the pivot hub for intercepting the vacuum port as aspirated fluid fills the chamber. As the fluid level rises, a light path is intercepted by the float to terminate aspiration. However, the float also mates with the vacuum port to close off the flow path. Thus, the system prevents overfilling of the container if the optical detector fails. So that filling of the cassette can be anticipated, a float space containing a second float is located along the proximal edge of the cassette. Finally, the bottom wall section includes a sterilization port which allows a cleaning system to inject a presterilizing fluid through the interior of the cassette to thereby cleanse all parts of the unit.

10 Claims, 4 Drawing Sheets

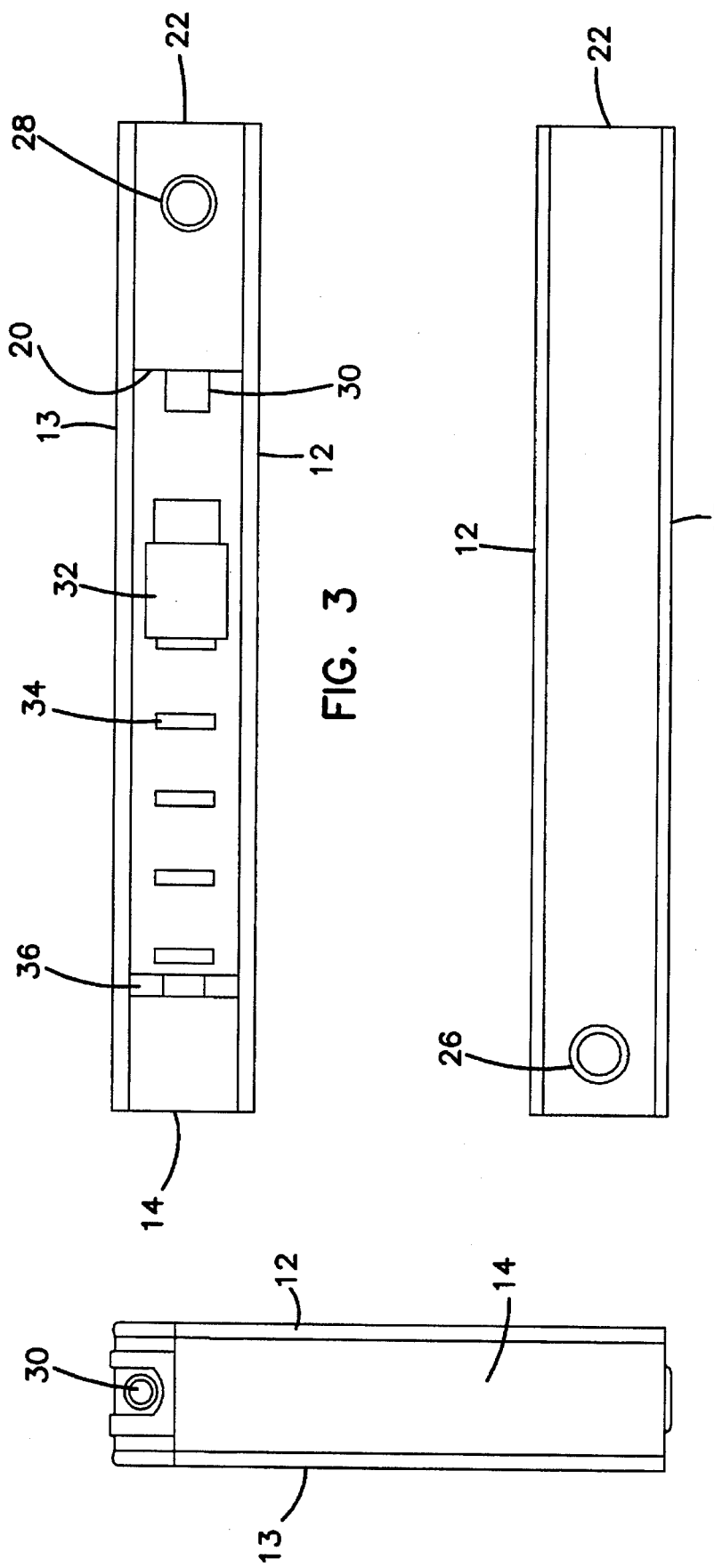

CASSETTE FOR RECEIVING ASPIRATED FLUIDS

FIELD OF THE INVENTION

This invention relates to cassettes, canisters and containers for receiving aspirated fluid in instrumentation systems used in surgical procedures, and more particularly to such canisters, cassettes and containers that may be reused, or treated as disposables.

BACKGROUND OF THE INVENTION

In a number of surgical procedures, such as ophthalmic procedures, the surgical site is irrigated during operation with a sterile solution, which is then drawn off (aspirated) under suction and collected in a container. In some systems, the vacuum is created in the container and a line from the surgical site leading to the container provides the aspirated fluid flow. The surgeon or a member of the operating staff has instrument controls for on/off control of flow, which controls also include means for instantaneously blocking off flow at a flushing or reflux clamp when vacuum at the surgical site must be terminated.

A number of products for this purpose are available that use different configurations, although they generally employ a container that is insertable in or attachable to the machine, and they are also arranged to reduce the number of attachments that have to be made. Older systems for surgery and ophthalmology were based on the use of separate tubing sections which had to be threaded into the machine, but most later systems incorporate a housing or body with attached or internal tubing, and an associated or attached collector or container. Since the systems must handle body fluids, one objective has been to provide low cost units which can be disposed of after use, which is generally the practice in the United States. In other countries, and with increasing attention to health care costs, some health care facilities prefer sterilization and reuse. In any event, the unit should be as low in cost as is consistent with operative and quality constraints.

One example of such a system is shown in U.S. Pat. No. 4,773,897 to Scheller et al., which is said to be a reusable autoclavable vessel, and is based upon a relatively thin vessel shape which fits into a recess in the machine with which it is to be used. The top wall of the container is specially shaped to provide a vacuum port adjacent its distal end, and includes an interior aspiration port, to which coupling is made by an insert. The insert fits within a recess in the top wall to be flush with the top wall, and the insert also includes a tubing extending in the proximal direction through the front wall of the housing. In order for this to be conveniently useable, the insert includes a breakaway portion and has a configured finger grip at its side. As the container fills, the level of fluid is detected by the system, which has a light path that is interrupted by a float ball contained in an interior chamber within the collector.

In addition to features of convenient connection at low cost, a number of desirable aspects should be provided in addition to the functions of flow control mentioned above. The interior of the chamber in the Scheller et al. device is not conveniently adequately cleaned and sterilized by autoclaving or otherwise, since the only two openings are close together, and the float in the interior chamber is not readily accessible to be cleaned and sterilized. In addition, the system only indicates when the canister is full, but the surgeon may prefer to observe the increase of fluid so that a decision can be made in anticipation of a need for replacement. Also, the system should assure, to the extent possible, that the aspirated fluid is not drawn into the vacuum system, which can happen as the liquid level rises toward the vacuum port. Finally, the system should include secondary means for preventing overfilling of the container in the event of a failure in the optical detection (light path) function.

SUMMARY OF THE INVENTION

Cassettes for collection of fluids in a fluid aspirating system in accordance with the invention have parallel broad sides spaced apart by a given spacing and joined by a peripheral edge wall having a top wall portion that is linear except for a raised distal end portion including a vacuum aperture adjacent the distal end wall. An aspiration port in an edge shoulder at the proximal end of the raised portion receives an aspiration tubing that extends along the top wall in the proximal direction for connection to means connecting to the aspiration site. Internally, means are disposed in the region of the vacuum port to increase flow impedance when the liquid level rises close the vacuum port, before shut off, so that liquid is not drawn into the vacuum port. The means for detecting the level is a loosely fitted pivot mechanism with a pivotable float at the free end that rides in a path to intercept the light path for the detector system, with its pivot end anchored loosely about a pin between the broad walls of the cassette. The peripheral proximal edge of the cassette is substantially transparent, and a space is defined by an associated interior wall that is parallel to the proximal edge, and a brightly colored float member is disposed in this space that is visible to a surgeon or operating staff during surgical procedures so that filling of the cassette can be anticipated. The flexible tubing leading proximally from the aspiration port includes a flexible flushing bulb which may be separately clamped, by a control mechanism in the system, against a backup surface on the top wall of the cassette. The opposite end of the aspiration tubing has a pair of spaced apart members which seat within an upstanding retainer at the proximal edge of the top wall.

In accordance with another aspect of the invention, the pivot arm mechanism and the pivotable float are disposed to restrict the vacuum port as the fluid level rises. To this end, the pivot is disposed near the cassette top wall, and the pivotable float is at a radius from the pivot such as to occlude the vacuum port, when fully raised, with a conforming top that mates in the vacuum port. An adjacent flag on the pivot arm intercepts the light path for the level sensor in this arrangement.

BRIEF DESCRIPTION OF THE DRAWINGS

A better understanding of the invention may be had by reference to the following description, taken in conjunction with the accompanying drawings, in which:

FIG. 3 is a top view of the arrangement of FIGS. 1 and 2;

FIG. 4 is an end view of the proximal end of the cassette of FIGS. 1 and 2;

FIG. 5 is a bottom view of the device of FIGS. 1–4, and

DETAILED DESCRIPTION OF THE DRAWINGS

Figure 1:
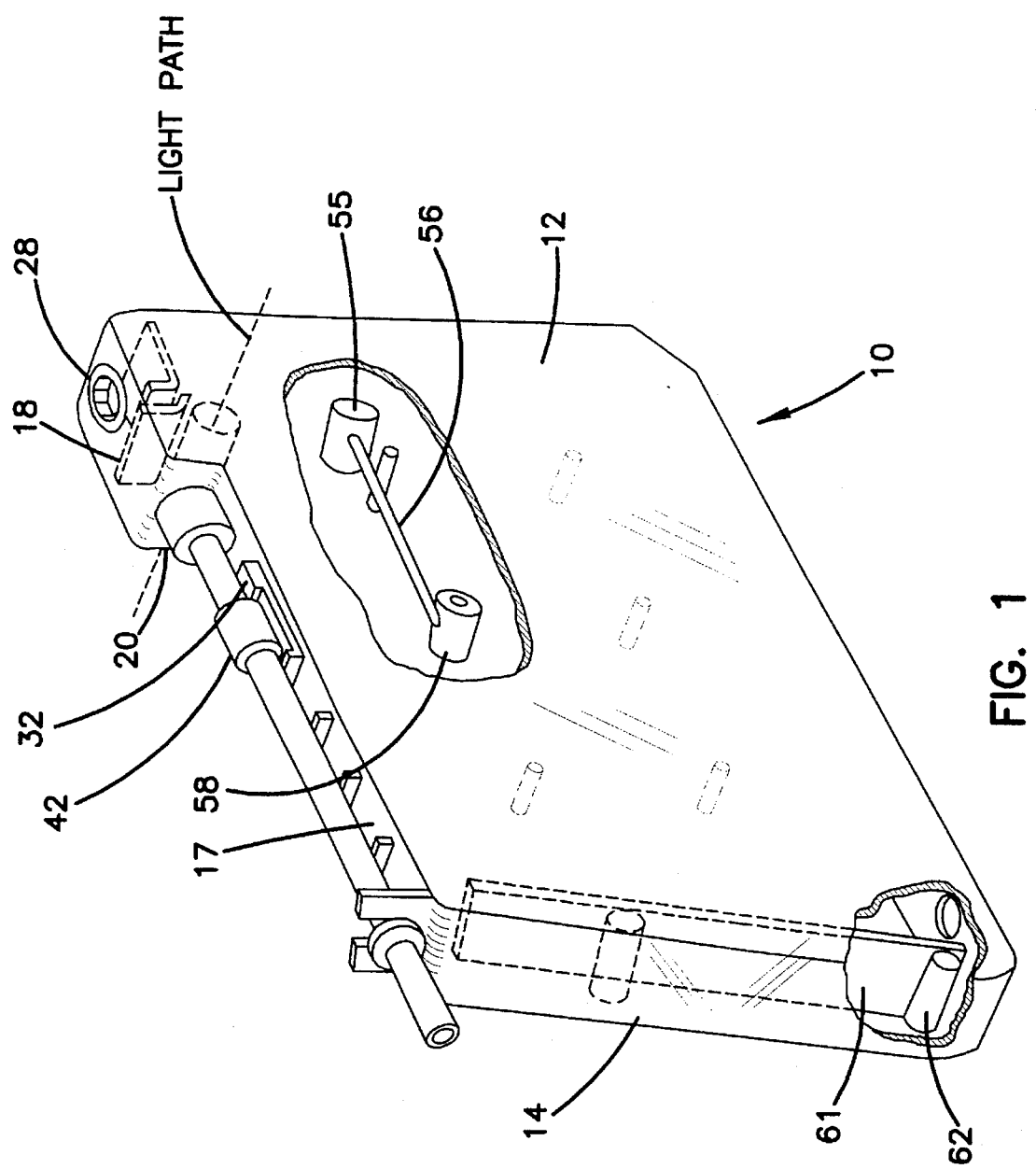
FIG. 1 is a broken away perspective view of a cassette for receiving aspirated fluids in accordance with the invention.

A cassette 10 in accordance with the invention, referring now to FIGS. 1–5, comprises a housing defined by a pair of broad side walls 12, 13, having a generally but not precisely rectangular outline, and joined together by a peripheral edge wall. The edge wall has different portions which may be manufactured in a single piece or in two or more joined sections, but comprises a proximal wall section 14 of transparent material, which may have indicia to indicate full fill level. The edge wall also includes a top wall having a principal portion 17 and, at the distal region thereof, a raised or projecting section 18 defining, at its proximal end, a vertical shoulder 20. The housing of the cassette is completed by a distal wall section 22, which is inserted first into the appropriate receptacle in the instrument, and a bottom wall section 24. The bottom wall section 24 includes a sterilization port 26 which is closed by a plug (not shown) during normal operation. The upper wall section 18 includes a vacuum port 28 adjacent the distal end of the cassette 10, which port 28 is to be engaged by the vacuum source in the associated instrument. At the shoulder 20, an aspiration port 30 protrudes outwardly in the proximal direction for attachment of an aspiration tubing. The principal portion 17 of the top wall 17 includes a backup surface 32 in an intermediate region, and a number of small support bars 34 spaced apart in the direction toward the proximal end, at which is disposed an upstanding retaining element 36 having a central slot. The aspiration tubing 40 has a distal end for seating in or on the aspiration port 30, a compressible flushing bulb 42 adjacent the backup surface 32 and engagable against it for closure. The tubing 40 also includes a pair of spaced apart radial rings 45, 46, which seat on opposite sides of the retaining element 36 when the aspiration tubing is placed in position.

Internally to the housing, a pair of baffle plates 50, 51, are placed in the region of the vacuum port 28. Without blocking the vacuum port 25, the baffle plates 50, 51 deflect aspiration flow downwardly and provide increased impedance to flow upwardly toward the vacuum port when the aspirated liquid approaches the fill level. As seen in FIG. 1, the light path for the level detection system transversely intercepts a region adjacent the vacuum port on the cassette 10, when the cassette is installed in the instrument. The light path is thus occluded, when the liquid level is at its desired maximum, by a pivoting float 55 on the distal end of a pivot arm 56. The opposite end of the pivot arm 56 is joined to a pivot hub 58 that fits loosely about one of a number of transverse pin spacers 60 between the broad walls of the cassette 10.

Adjacent the interior side of the proximal wall 14 is a parallel panel 61 which extends from adjacent the bottom wall 24 to adjacent the top wall 17 to define an open ended elongated inclined volume within which a bright proximal float 62 is confined. The bright float 62, visible through the transparent proximal wall 14, provides a visual indication of the level of liquid to the surgeon or other members of the operating staff.

In operation, the system of FIGS. 1–5 functions compatibly with a system of the type with which the Scheller et al. U.S. Pat. No. 4,773,897 operates. When the cassette 10 is inserted into the receptacle of the system, the vacuum port 28 is engaged, and a preconnected aspiration tubing 40, seated between the aspiration port 30 and the retaining element 36, is coupled to the surgical site via appropriate tubing (not shown). In this position, the surgeon can look through the proximal wall 14 to see the position of the bright float 62 and operate the controls, to establish a vacuum at will, or to clamp the line 40 at the flushing bulb 42, in known fashion. However, the tubing 40 is readily detached and disposed of if the cassette 10 is to be reused. As liquid fills within the interior chamber, it reaches the level of the pivotable float 55, which then continues to rise with the level, as does the bright float 62 at the proximal end. As the liquid level approaches the top wall 14, there is only a small interior volume to maintain under vacuum, and the impedance introduced by the baffles 50, 51, minimizes any tendency for liquid to be brought out. Ultimately, when the pivotable float 55 reaches the top level desired, the optical detection system shuts off further flow.

Figure 2:
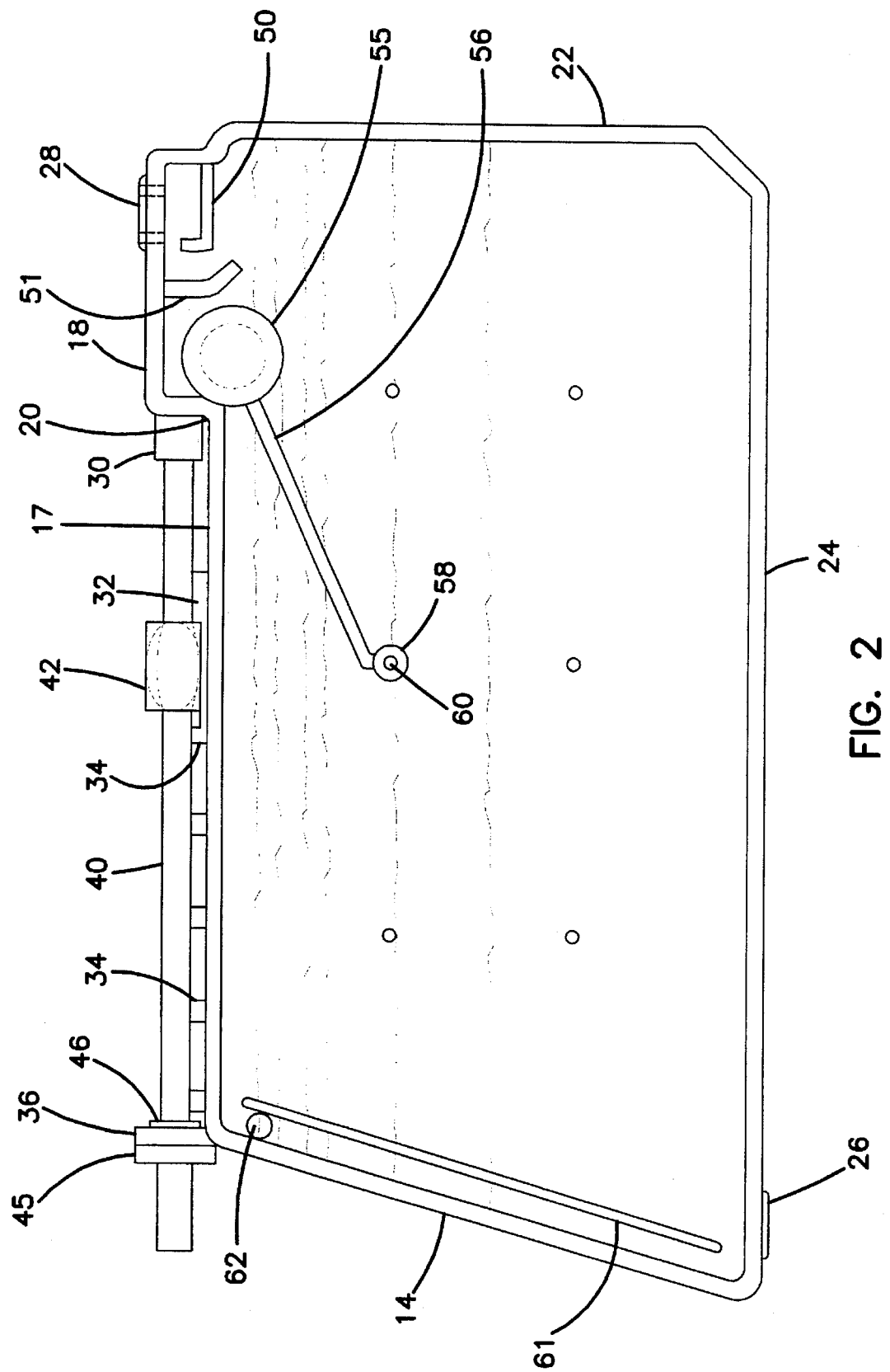
FIG. 2 is a side view of the cassette of FIG. 1, shown as with the face plate removed and substantially filled with aspirated fluids.

If it is then desired to reuse the cassette 10 after emptying the contents, the plug (not shown) in the bottom sterilization port 26 is opened, and both the aspiration port 30 and vacuum port 28 are opened, so that a high temperature, high volume flow in a presterilization cleaning system through the interior of the cassette 10 penetrates all parts of the unit. As seen in FIGS. 1 and 2, the panel 61 for containing the bright float 62 terminates short of both the top and bottom walls, leaving a space adequate for flushing out the interior volume between it and the front wall 14. This panel can also include slots for enhancing the flow, as long as there is no opening large enough for the proximal float 62 to escape. Back or reverse flows with ultrasonic agitation can be used for thorough cleaning of the pivot, the pivot arm and pivotable float, and the bright float. The unit can then be autoclaved for sterilization. In any event, the cassette 10 can be used only once and disposed of without significant cost penalty.

Figure 6:
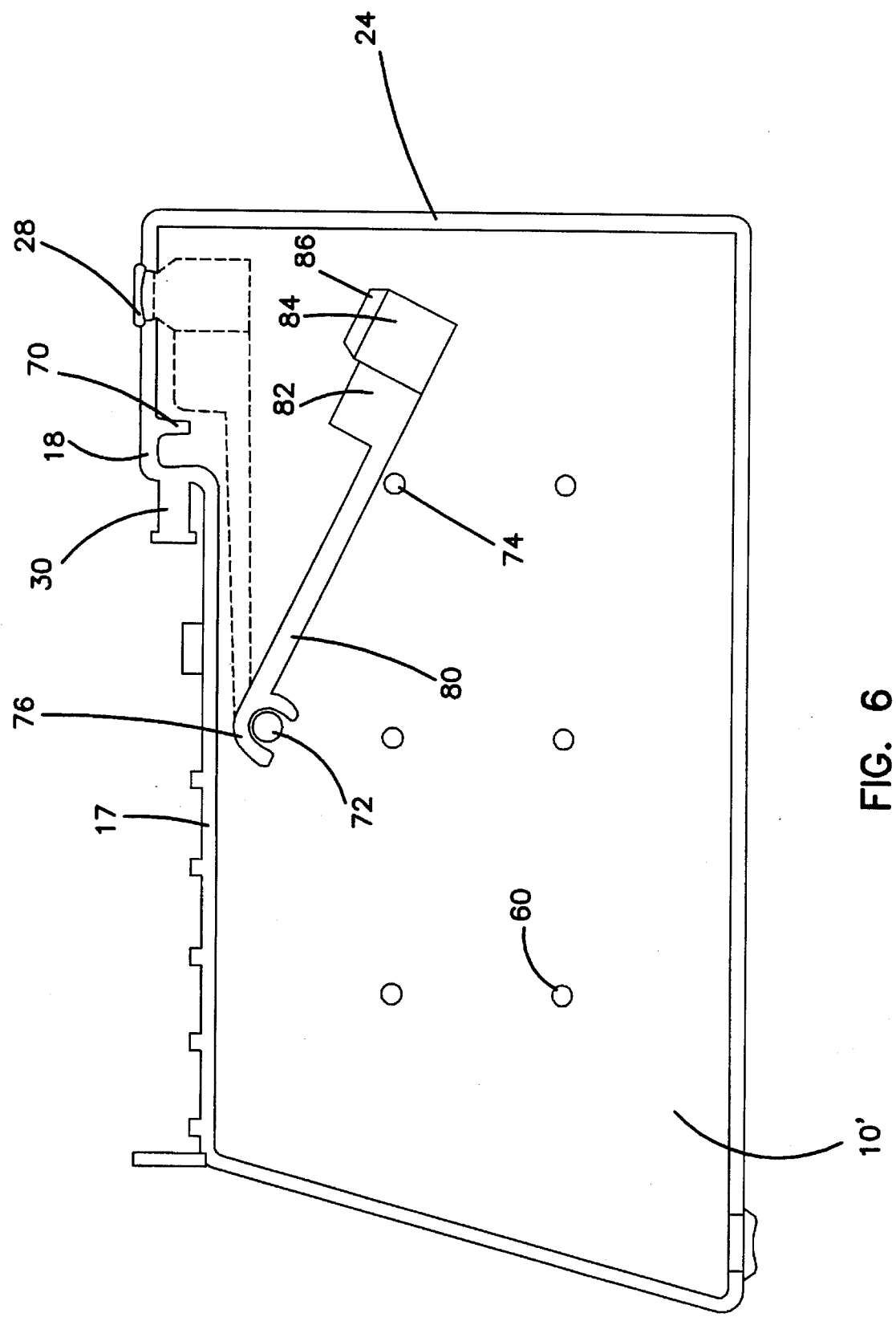
FIG. 6 is a side view, in section, of an alternative version of a cassette in accordance with the invention.

A cassette 10' in accordance with an alternate exemplification of the invention, referring to FIG. 6, comprises a housing having a wall defined by configurations substantially as described for and shown in FIGS. 1–5, and similarly numbered where like elements are used. An aspiration baffle plate 70 projects inside the chamber downward from projecting section 18 just distal to the aspiration port 30. The transverse pin spacers 60 between the side walls include a transverse fulcrum pin 72 near the top wall 17 and a transverse stop pin 74 near the distal wall 24. A generally U-shaped pivot hub 76 fits loosely around the fulcrum pin 72 and is attached to a pivot arm 80. At the distal end of the pivot arm 80 are, sequentially, a sensor flag 82 and a terminal, pivotable float 84. The terminal float has, at its top surface, a vacuum plug 86 conforming in mating fashion at its top surface to the vacuum port 28.

In operation the system of FIG. 6 functions compatibly with a system of the type described above, and in a manner generally similar to the operation of the system of FIGS. 1–5. That is, as the liquid level rises the impedance to flow toward the vacuum port 28 increases, opposing any tendency of liquid to be drawn into the port 28. Moreover, the system of FIG. 6 also will passively block the further application of vacuum to the cassette 10 chamber after the fluid has reached a critical level without requiring a decision by the physician or technician operating the system and also without requiring any function of the light detection means of the system. As the fluid level in the cassette 10' rises past the level of the stop pin 74, the terminal float 84 begins to rise also. At a critical level, the sensor flag 82 occludes the light path, causing a shutoff of the vacuum applied to the chamber. If the light path shutoff mechanism has malfunctioned or has been overridden, however, the vacuum plug 86 nevertheless eventually rises to create a seal with the vacuum port 28, thus preventing the further application of vacuum to the cassette 10' chamber and also preventing overflow from the chamber into the vacuum pump of the system. The aspiration baffle plate 70 prevents fluid entering the chamber of the cassette 10' through the aspiration port 30 from possibly occluding the light path or from unwanted entry into the vacuum port 28. Of course, those skilled in the art will recognize that a panel located parallel to the proximal wall and a proximal float for providing a visual indication of fluid level, as describe with reference to FIGS. 1–5, could be incorporated into this alternative embodiment. However, for simplicity, such an arrangement is not shown in FIG. 6.

In countries where the costs of medical supplies and instruments are prohibitive, a need exists for reusable system components, and also for means of extending the life of expensive instruments beyond the first malfunction of certain subcomponents. The alternate example of the invention allows for compatible function with the system Of the type with which the Scheller patent operates, but this version will continue to work even if the optical sensing means of the system malfunctions.

The invention described is an inexpensive disposable or reusable fluid container for use with a vacuum aspiration system. It provides for easy detection of fluid level through the clear proximal wall by means of the bright float. The invention makes possible easy and inexpensive cleaning and reuse by high volume flow-through cleaning using the vacuum, aspiration, and sterilization ports. An alternative exemplification of the invention also allows passive turn-off of vacuum to the chamber, by means of the terminal float as a plug to the vacuum port. This feature allows for the possibility to use the machine of the system even after a malfunction of the light path detection means.

We claim:

1. A cassette which may be reusable after sterilization, for collection of fluids in a fluid aspirating system comprising:

a housing defining an internal chamber for receiving fluid, the housing having broad parallel sidewalls from a proximal exterior end to a distal end to be engaged to the fluid aspirating system and peripheral walls joining the sidewalls, the peripheral walls including a top wall having a partially raised surface adjacent the distal end with a spaced apart proximal edge defining a shoulder, the shoulder including an aspiration port open in the proximal direction, the upper wall at the partially raised surface including a vacuum port therein;

aspiration tubing means releasably coupled to the aspiration port and extending externally along and adjacent the top wall in the proximal direction for connection to an exterior means for accessing the surgical site, the tubing means being compressible against the top wall at an intermediate region therealong;

pivot pin means fixed within the interior of the chamber defined by the housing; and level indicator means disposed within the chamber and including pivot hub means rotatably engaging the pivot pin means to pivot thereabout, arm means coupled at a first end to the pivot hub means, the arm means extending in the distal direction from the pivot hub means and a distal float means coupled to the distal end of the arm means and rising with the fluid surface as the fluid level increases in the chamber.

2. A cassette as set forth in claim 1, wherein the housing has an angled proximal edge wall of transparent material, a retainer wall spaced apart from, but parallel to, the proximal wall within the chamber interior, at a distance sufficient to allow passage of a proximal float means therebetween, and a proximal float means between the proximal edge wall and the retainer wall, whereby the proximal float means may be viewed through the front wall to provide an indication of fluid level in the chamber, and wherein the bottom peripheral wall of the housing includes port means that may be opened for sterilization of the chamber interior.

3. A cassette as set forth in claim 2 above, wherein the aspiration tubing means includes a flexible flushing bulb in an intermediate region thereof, and wherein the cassette further includes a backup surface on the top wall of the housing adjacent the flushing bulb for enabling the external compression of the flushing bulb, and wherein the cassette further includes flow impedance means disposed within the chamber in the region of the raised upper wall portion providing a constricted flow path adjacent the vacuum port, such as to minimize the tendency of fluid to be drawn into the vacuum port as the liquid level rises.

4. A cassette as set forth in claim 3 above, wherein the pivot hub means is relatively loosely disposed about the pivot pin means, and wherein the cassette means further includes upstanding retainer means having a substantially U-shaped slot adjacent the proximal end wall of the housing, and wherein the aspiration tubing means includes means for engaging the retainer means at the slot to hold the aspiration tubing means in position.

5. A cassette as set forth in claim 1 above, wherein the pivot hub means engaging with the pivot pin means is generally U-shaped, said pivot hub means being disposed within the interior of the chamber adjacent the upper wall and wherein the arm means and distal float means are configured such that the distal float means engages the vacuum port from within when fully raised, the pivotable float means having an upper surface configured to seal the vacuum port at full engagement.

6. A cassette as set forth in claim 5 wherein the level indicator means includes a planar element defining a detectable flag means extending upwardly from the arm means, said flag means being adjacent to the distal float means on the proximal side thereof.

7. A cassette as set forth in claims 5 or 6 wherein the housing has an angled proximal edge wall of transparent material, and a retainer wall spaced apart from, but parallel to, the proximal wall within the chamber interior, at a distance sufficient to allow passage of a proximal float means, whereby the proximal float means may be viewed through the front wall to provide an indication of fluid level in the chamber, and wherein the bottom peripheral wall of the housing includes port means that may be opened for sterilization of the chamber interior.

8. A cassette as set forth in claim 7 above, wherein the aspiration tube includes a flexible flushing bulb in an intermediate region thereof, and wherein the cassette further includes a backup surface on the top wall of the housing adjacent the flushing bulb for enabling the external compression of the flushing bulb, and wherein the cassette further includes flow impedance means disposed within the chamber in the region of the raised upper wall portion providing a constricted flow path adjacent the vacuum port, such as to minimize the tendency of fluid to be drawn into the vacuum port as the liquid level rises.

9. A cassette as set forth in claim 8 above, wherein the cassette means includes upstanding retainer means having a generally U-shaped slot adjacent the proximal end wall of the housing, and wherein the aspiration tubing means includes means for engaging the retainer means to hold the aspiration tubing means in position.

10. In a cassette arranged with a chamber having a top wall with a vacuum port by which a negative pressure can be established to draw aspirated fluid into the chamber, the combination comprising:

a pivot mechanism including a pivot hub spaced apart within the chamber from the vacuum port and a pivot pin attached to the chamber at a pivot axis, the pivot hub being disposed adjacent the top wall and including a generally U-shaped pivot hub member about the pivot pin, the pivot mechanism also including a pivot arm extending from the pivot hub in a direction toward the region of the vacuum port, a float disposed on the pivot arm at a radius to intercept the vacuum port, the pivot arm float being movable with aspirated fluid in the chamber and being configured to mate with the vacuum port to close off the flow path, when the fluid reaches a predetermined level, and a planar element on the pivot arm defining a detectable position flag for providing a visible indication of the level in the chamber.

* * * * *